United States Patent [19]

Tuason

[11] Patent Number: 5,403,330
[45] Date of Patent: Apr. 4, 1995

[54] SUTURE KNOT PUSHER

[76] Inventor: Leo B. Tuason, 135 Amanda Ave., Martinsville, Ind. 46151

[21] Appl. No.: 914,539

[22] Filed: Jul. 17, 1992

[51] Int. Cl.$^6$ ............................................. A61B 17/00
[52] U.S. Cl. ..................................... 606/148; 606/144; 606/139
[58] Field of Search ................ 606/144, 148, 139, 101

[56] References Cited

U.S. PATENT DOCUMENTS 2,595,086  4/1952  Larzelere ............................. 606/139
5,087,263  2/1992  Li ....................................... 606/148

Primary Examiner—Stephen C. Pellegrino
Assistant Examiner—Gary Jackson

[57] ABSTRACT

An improved laparoscopic suture knot pusher or a ligator comprising an elongated and slender shaft with both ends having specific functions. One end serves as the handle and the other is knot pusher forward guide end. The forward end tip is slightly convexed and has three hallowed-out spaces which receives and engages the throws and strands when the throw knot rundown process is activated delivering the throw knots through a trocar and tied intracorporeally at the surgical site. A method of knot tying is described in which a plurality of throws are executed all at one time extracorporeally on the two strands of the suture urging forward each throw knot in succession without a pause thereby eliminating the formation of loose knots but instead square knots are created and tightened at the surgical site.

4 Claims, 2 Drawing Sheets

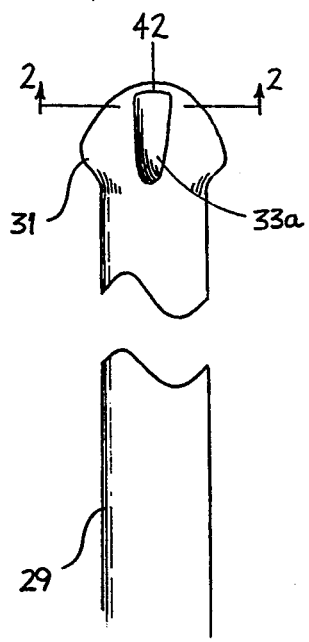
FIG. 3
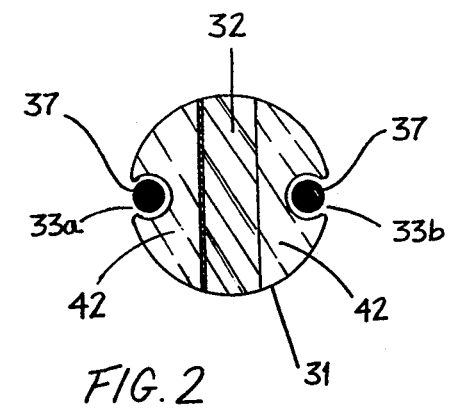
FIG. 2
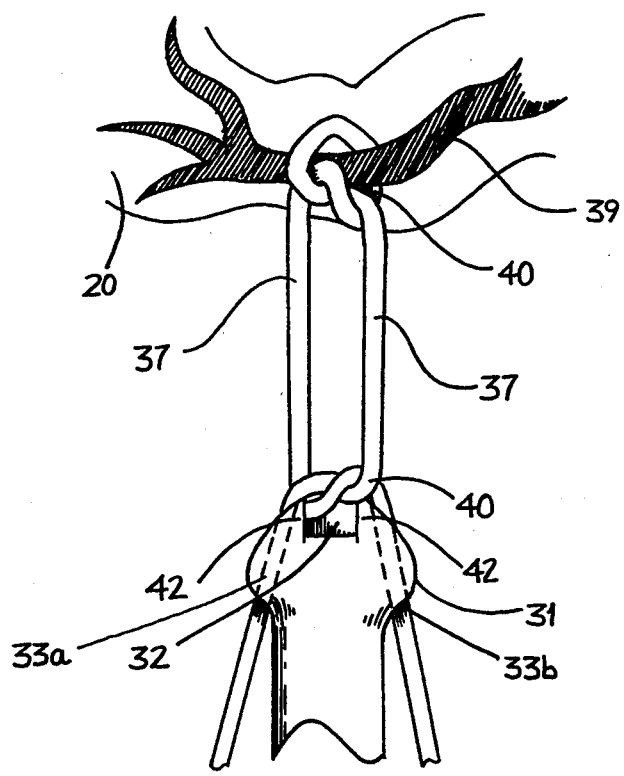
FIG. 1
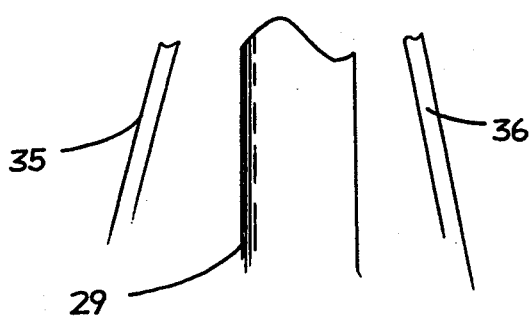
FIG. 4
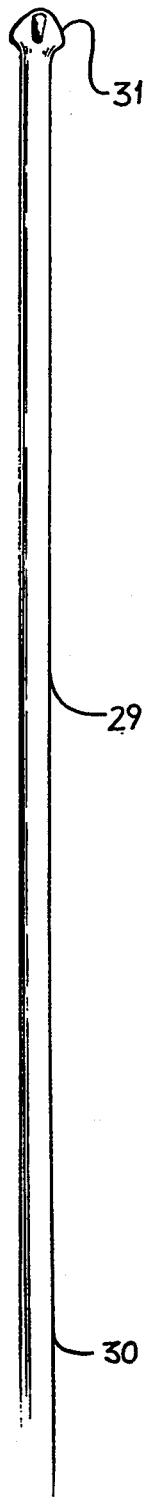

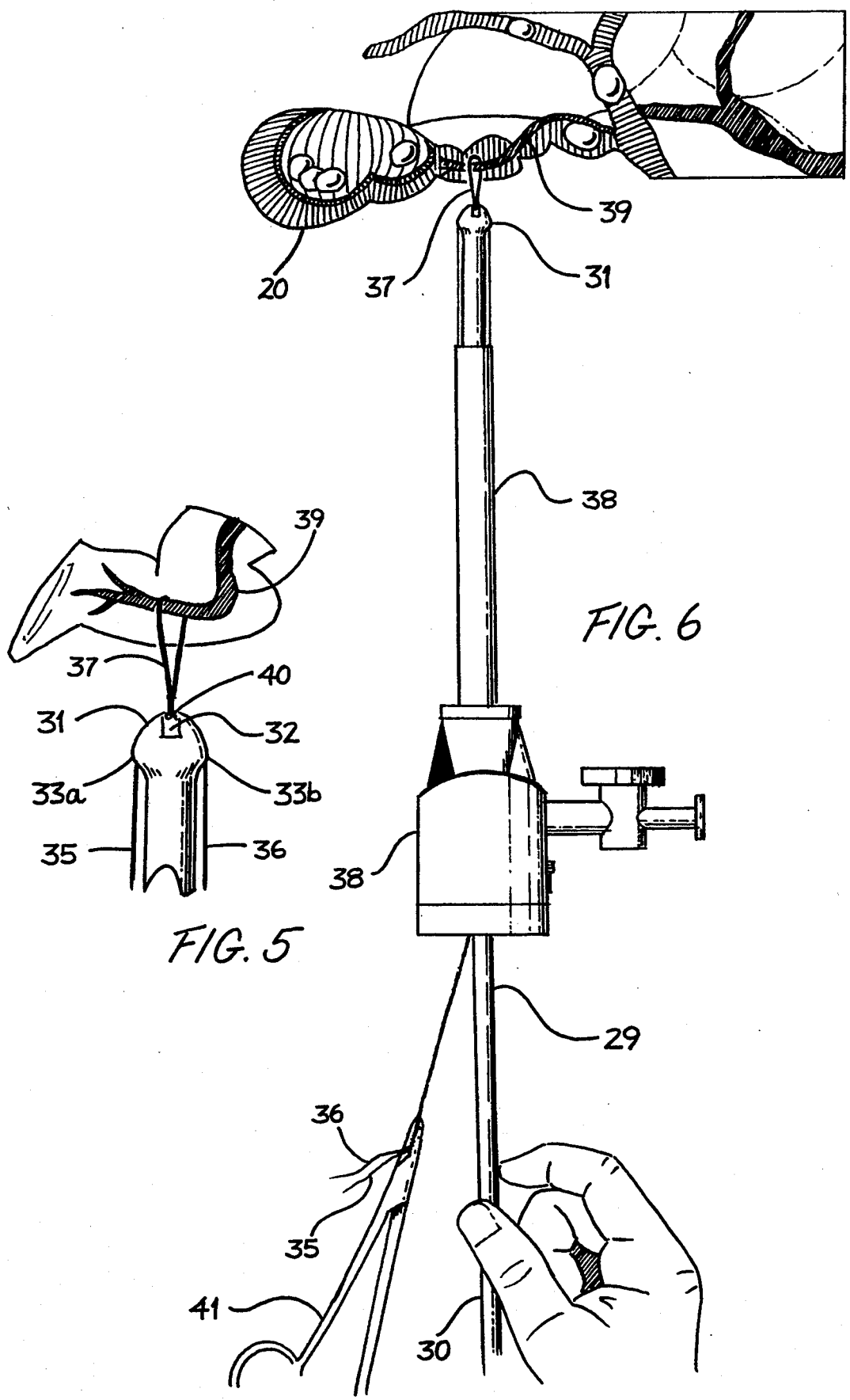

1

SUTURE KNOT PUSHER

FIELD OF INVENTION

The present invention relates to a surgical instrument or a device for securing blood vessels, ducts, bleeding areas and approximating tissues in parts of the body inaccessible to the surgeons hands when performing the high-tech VIDEO ASSISTED MINIMALLY INVASIVE ENDOSCOPIC SURGERY. It is a means that can deliver a ligature of plurality of suture throws initially fashioned extracorporeally (outside body cavity) and push these throws down and forward in succession without the need of a pause to tie another throw to the intracorporeal (inside body cavity) from whence the suture or ligature originated and anchored.

BACKGROUND OF THE INVENTION

Endoscopy is defined as a direct visualization of body cavities by the use of an instrument called ENDOSCOPE (a telescope with a built-in light for illumination). When the body cavity of the abdomen is entered during the operation, it is called LAPAROSCOPY, on the chest cavity it's THORACOSCOPY and the lower abdomen or pelvic region it's called PELVISCOPY.

The early beginning of ENDOSCOPIC SURGERY took place in Europe and pioneered by Gynecologists where they performed tubal ligations, removal of ovarian tumors or cysts, lysis of adhesions and as a diagnostic procedure. Some of these surgeons were brave enough to remove the appendixes through ½ inch abdominal incisions.

It was the successful and safe removal of the appendix that led the aggressive and innovative general surgeons to explore tile vast potential of the new surgical technology. Thus, the removal of the gall bladder or Laparoscopic Cholecystectomy was first performed in 1987 and only attracted minor curiosity. General surgeons were slow in accepting this new video assisted surgery but the procedure crossed the Atlantic in the early 1988 and thereafter several U.S. Surgical Centers began using this new operative technology with unerring success. The Laparoscopic Cholecystectomy has now become a standard operative procedure in removing a disease gall bladder.

In the first few years of Laparoscopic surgery, surgeons have encountered procedural difficulties. One difficulty is securing bleeding blood vessels, ducts and soft tissues. Several instruments and innovations to secure blood vessels were developed through the years and some are new like stapling divices, Laser coagulation and Electrocoagulation. There are also knot pushers with distinct individual features capable at securing bleeders but have significant drawbacks in some instances.

Devices like vessel clips and staples can stop bleeding points from small size vessels but sometimes not effective when dealing with larger caliber vessels. A vessel clip can not be used on bleeding flat surface. Likewise, the Laser and Electro-coagulation are limited on their efficacy to small vessels or ducts. Collateral burns to adjacent tissues or organs remote from the bleeding site may become a serious complication.

There are several Laparoscopic ligators or knot pushers presently being used have individual drawbacks in securing bleeding site or potential bleeder. One such knot pusher is made of plastic shaft with a central channel where suture is threaded into the entire length of the shaft and in the forward end has a preformed knotted loop, the latter anchored and looped around the bleeding vessel or potential bleeder and the knot is pushed and tightened against the surgical site. A slip knot is always formed by this device or any other tools using the preformed knotted loop and could not be used in larger caliber vessels or ducts and bleeding flat surface where there is no 'pedicle' to anchor the loop.

Devices or tools that uses preformed knotted loop has another drawback in that when the knot is run down to the surgical site there is a 'sawing' action of the ligature on the tissue or vessels causing tear, a serious complication. An added drawback on devices with preformed knotted loop is that the free end of the suture must be threaded through a hole at the guide end of the tool after each throw has been delivered to the surgical site and this can be time consuming and also requires an assistant to perform the task.

Another type of knot pusher have a pair of spaced arms forming a circular opening for guiding the suture permits easy slipping of throws fashioned extracorporeally to the surgical site but a skew tension must be applied on either knot tether. The lateral tension necessary to tighten the knot posses the danger of inadvertent injury to adjacent organs. These devices can only produce slip knots so that the surgeon must deliver more than three throws in succession to comfortably secure the bleeder or tissue.

Some of the knot pushers currently used in Laparoscopic surgery are selective on the suture material that each tool can readily slide the throws smoothly to the surgical site. There are devices that have difficulty in sliding two intertwine of monofilament sutures and when pressure is applied on the throw, it gets stuck to the guide end.

It is imperative to create square knots from two or three run down throws tightened on top of each other against the vessel being shut off or two opposing tissues being approximated or sutured. The square knot (nonslip) is unyielding to the internal pressure of a vessel undoubtedly more desirable surgical knot in securing tissues. To develop a square knot, the surgeon must maintain tension on the suture ends while creating throws and sliding them with the pusher to the surgical site. If the tension is not maintained appropriately, loosening of the knot takes place a situation which would be detrimental in securing of the tissue involved. Surgeons using the standard maneuver of sequential throw—run down—throw will not be able to maintain the necessary tension and as a result a loose knot is formed.

OBJECTS AND SUMMARY OF THE INVENTION

Key Words and Definition

Intertwine—when two free ends of the suture material are looped over one another once or twice.

Throw—one or more intertwine.

Knot—two or more throws laid in succession on top of each other and finally tightened and secured.

Conventional Knots used in Surgery

Surgeon's knot—two intertwines delivered first to the surgical site with a 'holding' effect thus preventing the loops from disentanglement.

Slipknot—a knot which allows the loop to tighten when one strand is drawn.

Square knot—two throws run down in succession to the surgical site, one sitting on top of the first and tightened. This knot is the most desirable in securing tissues because once tightened it remains fixed and unyielding to applied pressure, like the internal pressure of blood vessel or opposing tissues.

Intracorporeal—inside body cavity
Extracorporeal—outside body cavity

The Video Assisted Minimally Invasive Laparoscopic Surgery is a new surgical technology which has completely changed the operative approach to some problems encountered inside the body cavity where one half inch incisions on the abdominal or chest walls are used instead of the traditional or open technique of five to six inches incisions to enter the cavity. In the new laparoscopic surgical procedures, it requires the use of long slender instruments to reach the surgical sites by manipulating and guiding said instruments extracorporeally.

Because of the limited access to the surgical site when performing laparoscopic surgery, devices like the present invention are developed to help facilitate knot-tying thus an object of the present invention is to provide a means by which these throw-knots are delivered or run down smoothly through the trocar-instrument port and finally tightened and secured at the surgical site. In addition to the above throw-knot delivery system, a method is developed in which several throws usually three or four, spaced 1 inch apart and fashioned extracorporeally on the two strands of the suture or ligature previously anchored at the surgical site.

Another object of the present invention is to provide a system of creating surgical knots by initially forming in a linear manner several throws appropriately spaced on the two strands of the suture or ligature and finally all of these extracorporeally fashioned throws are individually urged forward with precision and dispatch without pause to the surgical site by the knot pusher while an amount of tension on the free ends of the suture is maintained.

Yet another object of the present invention is to provide a method in which a plurality of throws are executed all at one time extracorporeally on the two strands of the suture anchored and originating from the surgical site and with the surgeon's fingers helping to steady the loops formed by the throws while the other hand engages the guide end of the knot pusher behind each throw and then run down in succession to the surgical site.

Surgeon's hands are nolonger in direct contact with body tissues when performing knot-tying maneuvers in the new laparoscopic surgery.

Still another object of the present invention is to provide an improved laparoscopic ligator which can be utilized for tying ligatures on blood vessels, ducts and bleeding tissues in areas inaccessible by the surgeon's fingers.

To achieve the final goal of creating a fixed surgical knot, i.e. square knot would therefore need a method or technique by which several throws are formed first extracorporeally, aligned and adequately spaced one after the other on the strands of the suture or ligature are held in appropriate tension and a rundown system to deliver the throws in succession without pause to the surgical site. The above objectives are being provided by the present invention and many more unique features unfold as the knot-tying process continues.

It is clear and evident that the present invention has proven to have advantages over the other suture ligators which would make it more preferable for a surgeon to use.

The fact that the present invention has clearly shown it's throw knot rundown capability on multiple intertwine throws like the surgeon's knot delivering these knots with extreme ease to the surgical site, a feat that most of the other ligators can not accomplish, makes this device more desirable. Another important advantage of the present invention demonstrates it's ability of creating plurality of throws, extracorporeally fashioned, appropriately spaced throw knots on two strands of the ligature or suture (thread with needle at one end) delivering these throws by means of the rundown system to the surgical site without pause thus eliminating the formation of loose knots.

Yet another advantage that one will recognize is inadvertent injuries caused by a 'sawing' action on tissues and damage to adjacent organs by the lateral skew tension when applied during knot tying is not eminent in the present invention. This is common to ligators using preformed knotted loop ligatures. Threading of the ligature through the holes provided at the guide ends of ligators is difficult and time consuming and requiring an assistant to do the task are altogether eliminated in the present invention.

Another advantage of the present invention is it's efficiency in the throw knot delivery system and the sliding motion of the device is smoother than most of the ligators. Furthermore, the present invention requires just one surgeon to perform the throw knot delivery and uses only one tool, the knot pusher to accomplish the process. Some ligators requires a second tool, a suture throw holder which most likely needs an assistant in the preparation of multiple suture throws set on the throw holder.

Still another advantage of the present invention is the simplistic construction of the knot pusher device has added to it's appeal to the operating room staff because of easier maintenance. There are ligators that are relatively complexed in construction and have moving parts which makes them more vulnerable to the effects of wear and tear, thus breakage of parts might take place intracorporeally and retrieval of broken metal piece might be extremely difficult. The present invention has none of this mishap and the knot pusher has no mving parts.

Cleaning of the more complexed instruments with moving parts is difficult and time consuming as one would expect a thorough inspection and removal of all crusted old blood from tiny recesses in the tool is mandatory.

Finally, surgeons will witness how efficient the present invention functions in the formation of desirable fixed, unyielding surgical square knots on most of the suture materials, like the monofilament nylon, chromic catgut, braided black silk and other synthetic suture materials.

BRIEF DESCRIPTION OF THE DRAWINGS

A full account of the construction of the present invention and presenting the inherent characteristic features of the instrument device are depicted in the accompanying drawings and a view of rundown or delivery system is noted.

FIG. 1 is a side elevation view of the surgical instrument, a laparoscopic ligator of this invention.

FIG. 2 is a sectional view taken substantially along the line 2—2 of FIG. 3.

FIG. 3 is an enlarged fragmentary longitudinal section view of the instrument, which is called suture guide end showing one of the two lateral grooves.

FIG. 4 is a fragmentary enlarged section of suture guide end of the instrument showing the relationship and arrangement of the two strands of the suture each engaged in the lateral grooves and a knot about to be pushed and laid over the first knot at the surgical site. This also constitute a phase of the rundown or delivery system.

FIG. 5 is an enlarged fragmentary perspective view showing the suture guide end with the engaged suture strands in the lateral grooves and a knot being pushed to the surgical site in this instance the blood vessel of the gall bladder.

FIG. 6 is a fragmentary perspective view showing the instrument device pushing the throw knot through the trocar delivering the same to the surgical site and the relationship with the hand manipulating the device extracorporeally and the free ends of the suture held taut by a hemostat.

DETAILED DESCRIPTION OF THE INVENTION

The laparoscopic instrument in essence a ligator 29 in FIG. 1 consists of an elongated shaft made of stainless steel rod preferably small outside diameter size having both ends different in configuration with specific function. One end of the shaft 29 is the suture guide or spheroidal pusher member 31 and the opposite end is the handle 30 in FIGS. 1–6. The forward end of the shaft 29 is spheroidal shaped member which is slightly convex and here are located three hollowed-out spaces thereon. One of these recesses is a slot 32 in FIGS. 2-3-4 cut across the middle of the convexed surface at a depth of 1 mm and 1 mm wide, a cutout space large enough to accommodate a portion of the formed throw in order to facilitate a smooth sliding motion or advancement of the instrument. Without this cutout space slot 32, the suture throw tends to get stuck and binds to the forward end during the rundown process.

Also at the forward end of the shaft 29 are the other two hallowed-out spaces or grooves 33a and 33b in FIGS. 2-3 both runs to a very short distance from the tip of the forward end longitudinally and parallel to the shaft 29. The two lateral grooves 33a and 33b are diametrically opposite each other located at right angle to the midsection of the slot 32 but not transecting the latter. There is a smooth narrow ridge 42 in FIGS. 2-3-4 formed in the vicinity of of the midsection of slot 32 separating each groove 33a or 33b from slot 32 and this is well demonstrated in FIG. 4. The grooves 33a and 33b shown in FIG. 2 have adequate cutout spaces to accommodate loosely single strand to each groove during the throw knot rundown process.

The strategically located and fashioned slot 32 in relation to the two lateral grooves 33a and 33b and the intervening narrow ridges 44 allows a smooth sliding motion of the instrument as the surgeon engages the guide end of the device behind each throw knot and rundown in succession to the surgical site as noted in FIG. 4 where surgical square knots are finally formed.

The instrumentation in the performance of Laparoscopic Cholecystectomy (removal of diseased gall bladder) using the high-tech procedure is hereby presented to further demonstrate the function of the present invention. It will also show the mechanism of the throw knot delivery or rundown system and the final formation of surgical square knots. Similar delicate and precision laparoscopic instruments like the present invention can be used in both simulation of surgical technique on inanimate objects and on actual live operation, not limited to gall bladder but on tissues in the different body cavities.

The function of the present invention described below is illustrated in the laparoscopic surgery of the gall bladder wherein the invention is used to ligate or tie the cystic artery by the extracorporeal knot tying technique.

The initial step taken by the surgeon after all the proper preparation for surgery as we know it, is the insertion of the long needle into the abdominal cavity through the navel to distend the cavity with carbon dioxide passed through the needle from an automatic insufflator separating the abdominal wall from the organs thereby providing a better view and operating space.

A plurality of trocars are inserted through ½ inch skin incisions at different places on the abdominal wall will serve as portals or entry windows for the instruments. The laparoscope with it's integral systems of viewing optics, fiberoptic illumination and a video camera attached to the rear end of the endoscope is inserted through the navel trocar port.

In the extracorporeal knot tying, the ligature 37 in FIGS. 5-6 is first introduce into the body cavity by grasping the ligature free end 35 and pass it through the trocar port 38 as shown in FIG. 6. Once the free end 35 in FIGS. 5-6 has entered the cavity, it is grasped by tissue grasper and pass it around the blood vessel 39 in FIGS. 4-5-6 and then brought out of the cavity through the same trocar port 38 by a tissue grasper. Both free ends 35 and 36 of the ligature are outside the body cavity ready to execute the throw knot forward delivery system.

The free ends 35 and 36 of ligature 37 as shown in FIGS. 4-6 are intertwined once or twice forming throws and several more throws are fashioned extracorporeally most often three or four such throws spaced at one inch apart on the two strands of ligature 37. After the required number of throws are formed in a linear manner appropriately spaced on the two strands of the ligature, the surgeon's fingers helps to steady the loops formed by two adjacent throws while the other hand engages the guide end 31 in FIG. 4 of the shaft 29 to the strands of the loop behind each throw. The strands of each loop are received by 33a and 33b, one strand to each groove shown in FIGS. 2-4.

The first throw knot 40 in FIGS. 4-5-6 is now infront of the suture guide end of shaft 29 while the surgeon manipulates the handle of the instrument thus introducing it through the trocar port 38 in FIG. 6 to enter the abdominal cavity. The rundown process is continued by urging and sliding forward the throw knot while the appropriate counter tension on the free ends 35 and 36 held by a hemostat forcep is maintained as the throw knot is delivered to the surgical site, in this instance the artery of the gall bladder 39 shown in FIGS. 4-5-6. The rundown maneuver is repeated on the next throw knots individually urged and pushed forward with precision and dispatch without pause in succession set each throw on top of the other as shown in FIG. 4, the second throw knot about to settle on top of the first and finally a gentle pressure is applied on the knot pusher thereby creating a surgical square knot tightened and secured. The free ends of the strands few millimeters from the last throw are cut to complete the tying procedure.

The surgical scenario described above is one of many surgical procedures in which the present invention could be implemented and the previous description is in no way limit the utilization of the throw knot delivery system and the ligator device.

It must be emphasize at this point that in the creation of square knots, the throw knot rundown process of each throw is preceded by a gentle tug and a pull rearward of the free end 35 of the suture forcing the strand 36 to encircle or form a a loop around the strand 35, this being done alternately on both strands thereby creating throws that are precursor to the making of square knots.

The description and drawings of the present invention is hereby acknowledged as true in all aspect of it's functional design and should there be variance necessary involving the structural composite therein, it would still project the physical likeness of the original and remains within the realm of the invention's function

I claim:

1. A surgical instrument for tying ligatures and sutures comprising;
   a shaft member laving proximal and distal ends and having substantially constant cross sectional measurements along the shaft and longitudinal axis between said ends, one of said ends is a handle and the other of said ends is a suture guide or throw-knot pusher;
   said guide end having three hallow cut-out spaces, located thereon wherein one of said cut-out spaces is a slot that runs across a midsection of a slightly convexed surface having a spheroidal shaped configuration at said distal end of said shaft and said slot is dimensioned to accommodate a portion of a formed throw-knot of said instrument allowing a smooth motion of the instrument during a throw knot rundown process.

2. The surgical instrument of claim 1 wherein said guide end further having two hallow cut-out spaces or grooves situated longitudinally to the longitudinal axis of said shaft member and are diametrically opposite each other on either side of said slot, said longitudinal grooves are located at a right angle to said slot but not transecting said slot, said grooves are dimensioned to loosely accommodate single strands of said ligature in each said groove during the throw knot rundown process.

3. The surgical instrument of claim 1 wherein said guide member further having two narrow and smooth ridges located juxtaposed to the midsection of said slot separating said longitudinal grooves from said slot; said ridges assist in the throw knot rundown process, wherein said strands behind each throw straddles on top of said ridges causing said strand to slide freely as said instrument is pushed forward to the surgical site.

4. A method of knot tying a plurality of throw knots by providing an instrument of claim 1, each said throw knot being extracorporeally and sequentially fashioned at least 2 cm apart on two strands of a suture from a remote surgical site, whereby said throw knots are formed by executing a gentle pull rearward on one said strand forcing the other strand to encircle or loop around said pulled strand, thence engaging the strands behind each throw knots with the transverse slot and longitudinal opposing grooves of the distal end of said instrument of claim 7 and runing down each throw knot in succession through the lengths of suture to a predetermined surgical site.

* * * * *